United States Patent
Tong et al.

(10) Patent No.: US 11,203,663 B2
(45) Date of Patent: Dec. 21, 2021

(54) METHOD FOR SEPARATING PHA AND PHA PREPARED THEREFROM

(71) Applicants: COFCO (jilin) Bio-Chemical Technology CO., Ltd, Changchun (CN); Nutrition & Health Research Institute, COFCO Corporation, Beijing (CN); COFCO BIOTECHNOLOGY CO., LTD., Bengbu (CN)

(72) Inventors: Yi Tong, Beijing (CN); Yi Li, Beijing (CN); Fang Tian, Beijing (CN); Kejia Xu, Beijing (CN); Yuanheng Guo, Beijing (CN); Bo Chen, Beijing (CN); Tai An, Beijing (CN); Dayong Li, Changchun (CN); Haijun Liu, Changchun (CN); Lida Wu, Changchun (CN)

(73) Assignees: COFCO (jilin) Bio-Chemical Technology CO., Ltd, Changchun (CN); Nutrition & Health Research Institute, COFCO Corporation, Beijing (CN); COFCO BIOTECHNOLOGY CO., LTD., Bengbu (CN)

( * ) Notice: Subject to any disclaimer, the term of this patent is extended or adjusted under 35 U.S.C. 154(b) by 0 days.

(21) Appl. No.: 17/137,545

(22) Filed: Dec. 30, 2020

(65) Prior Publication Data

US 2021/0340316 A1    Nov. 4, 2021

(30) Foreign Application Priority Data

Apr. 29, 2020   (CN) .......................... 202010358326.7

(51) Int. Cl.
| | |
|---|---|
| *C08G 63/90* | (2006.01) |
| *C12P 7/62* | (2006.01) |
| *B01D 39/08* | (2006.01) |
| *B01D 21/26* | (2006.01) |
| *B01D 37/02* | (2006.01) |
| *B01D 1/16* | (2006.01) |

(52) U.S. Cl.
CPC .............. *C08G 63/90* (2013.01); *B01D 1/16* (2013.01); *B01D 21/262* (2013.01); *B01D 37/02* (2013.01); *B01D 39/08* (2013.01); *C12P 7/625* (2013.01); *B01D 2239/0471* (2013.01); *B01D 2239/06* (2013.01)

(58) Field of Classification Search
None
See application file for complete search history.

(56) References Cited

FOREIGN PATENT DOCUMENTS

| | | | |
|---|---|---|---|
| CN | 1328160 | A | 12/2001 |
| CN | 1464063 | A | 12/2003 |
| CN | 1844185 | A | 10/2006 |
| CN | 102492737 | A | 6/2012 |
| CN | 109504715 | A | 3/2019 |
| CN | 111019108 | A | 4/2020 |
| CN | 111346580 | A * | 6/2020 |

OTHER PUBLICATIONS

English language machine translation of CN 111346580 A, generated Mar. 2, 2021. (Year: 2021).*

* cited by examiner

*Primary Examiner* — David C Mellon
(74) *Attorney, Agent, or Firm* — Volpe Koenig

(57) ABSTRACT

Provided a method for separating PHA and PHA prepared therefrom. The method comprises the following steps: subjecting a PHA fermentation broth to solid-liquid separation to obtain a thallus precipitate; breaking cell walls of the thallus precipitate, and subjecting obtained wall-broken products to a plate and frame filtration to obtain PHA; a filter cloth for the plate and frame filtration is pre-coated with a PHA layer. The method adopts a plate and frame separation to replace the traditional centrifugal separation to prepare PHA, and the PHA layer is pre-coated on the filter cloth for the plate and frame filtration, thereby overcome the defects in the prior art such as high cost and operational difficulty caused by adopting multiple centrifugal separations; in addition, the method of the present disclosure also exhibits the advantages of high recovery rate of PHA and high purity of the prepared PHA product.

14 Claims, No Drawings

METHOD FOR SEPARATING PHA AND PHA PREPARED THEREFROM

PRIORITY CLAIM & CROSS REFERENCE

The application claims priority to Chinese Application No. 202010358326.7, filed on Apr. 29, 2020, entitled "Method for Separating PHA and PHA Prepared Therefrom", which is herein specifically and entirely incorporated by reference.

FIELD

The present disclosure relates to the technical field of preparing bio-based material Polyhydroxyalkanoate (PHA), in particular to a method for separating PHA and PHA prepared therefrom.

BACKGROUND

Polyhydroxyalkanoate (PHA) is a generic name for a kind of high molecular polyesters which are entirely synthesized by microorganisms. PHA has biodegradability and biocompatibility, thus the PHA is considered as an environment-friendly material, which is conducive for solving the problem of increasingly serious environmental pollution. Although the use of PHA can effectively avoid the harm caused by petrochemical plastics to the environment, PHA exists in bacteria and has complex components and is extremely difficult to extract. The commercial development of PHA has been constrained by its high separation cost. In order to improve economic benefits, the development of a separation method with low cost, high efficiency and high recovery rate is the only way for industrialization.

Most of the separation processes in prior art adopt a multiple centrifugal separation method, but the centrifugal separation method has the disadvantages such as low separation efficiency for a standalone machine, large energy consumption, high operative difficulty, and limited separation capability; it requires a plurality of centrifuges to operate simultaneously for large-scale industrialization, which results in the large amount of one-off investment on facilities and devices. What is more, with these separation processes in prior art, the PHA recovery rate is low and the purity of PHA particle products obtained is also low.

SUMMARY

The purpose of the present invention is to overcome the disadvantages of high PHA separation cost, low recovery rate, and low product purity in the prior art, and to provide a method for separating PHA and PHA prepared therefrom. It has the beneficial effects of low one-time investment, low production cost, high PHA recovery rate, and high purity of the obtained PHA product.

In order to fulfill the above purposes, in a first aspect, the present invention provides a method for separating PHA comprising the following steps:

subjecting a PHA fermentation broth to solid-liquid separation to obtain a thallus precipitate;

breaking cell walls of the thallus precipitate, and subjecting obtained wall-broken products to a plate and frame filtration to obtain PHA;

wherein a filter cloth for the plate and frame filtration is pre-coated with a PHA layer.

In a second aspect, the present invention provides a PHA prepared according to above method, and the PHA has a purity of at least of 90%.

The method adopts a plate and frame separation to replace the traditional centrifugal separation to prepare PHA, and the PHA layer is pre-coated on the filter cloth for the plate and frame filtration, thereby overcome the defects in the prior art such as high cost and operational difficulty caused by adopting multiple centrifugal separations; in addition, the method of the present disclosure also exhibits the advantages of high recovery rate of PHA and high purity of the prepared PHA product. As shown in the examples, with the method of the present invention, the PHA recovery rate is at least 80%, and the PHA product purity is at least 90%; under more preferable conditions, the PHA recovery rate and purity can be further improved.

DETAILED DESCRIPTION

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

In a first aspect, the present invention provides a method for separating PHA comprising the following steps:

subjecting a PHA fermentation broth to solid-liquid separation to obtain a thallus precipitate;

breaking cell walls of the thallus precipitate, and subjecting obtained wall-broken products to a plate and frame filtration to obtain PHA;

wherein a filter cloth for the plate and frame filtration is pre-coated with a PHA layer.

In the course of research, the inventor of the present invention found that using traditional plate and frame filtration instead of multiple centrifugation conventionally used in the prior art, although it can simplify operations and reduce costs, it also leads to a further reduction in the recovery rate of PHA, which are undesirable for those skilled in the art. However, the inventor of the present invention further discovered during the research that if the filter cloth for the plate and frame filtration is coated with PHA in advance, not only the recovery rate can be improved, but the purity of the PHA product can also be ensured.

According to the present invention, although the purpose of the present invention can be achieved by coating the filter cloth with conventional PHA, the inventors of the present invention found that the average particle size of PHA pre-coated on the filter cloth is larger than the average particle size of PHA in the wall-broken product, the recovery rate and purity of the obtained PHA product can be further improved.

Generally, the particle size of the PHA in the wall-broken product is 0.1-10 μm, preferably 0.3-5 μm. Preferably, the particle size of PHA pre-coated on the filter cloth ranges from 1 to 200 μm, wherein the PHA pre-coated on the filter cloth can be obtained commercially. It can be also obtained by grading and screening the products produced by the factory.

According to the present invention, the thickness of the PHA layer can be changed in a wide range. Preferably, in order to further improve the purity of the obtained PHA product, the thickness of the PHA layer is 1-30 mm, preferably 8-12 mm, for example, 8 mm, 9 mm, 10 mm, 11 mm, 12 mm.

According to the present invention, the pore size of the filter cloth pre-coated with the PHA layer is preferably 1-25 µm, preferably 2-10 µm, for example, 2 µm, 3 µm, 4 µm, 5 µm, 6 µm, 7 µm, 8 µm, 9 µm, 10 µm.

According to the present invention, the method of coating the PHA layer on the filter cloth is not particularly limited. For example, PHA can be mixed with water to prepare a suspension, and coated the suspension on the filter cloth, then dried to complete the coating of the PHA layer.

According to the present invention, the conditions of the plate and frame filtration preferably include: a temperature of 10-40° C., a pressure of 0.2-0.8 MPa, and a time of 1-8 hours; more preferably: a temperature of 20-35° C. (preferably 23-28° C.)), a pressure of 0.6-0.7 MPa, and a time of 3-5 hours.

According to the present invention, the method for solid-liquid separation of the PHA fermentation broth can be carried out in accordance with conventional operations in the art. However, the inventors of the present invention have found in research that when the solid-liquid separation includes a first solid-liquid separation and a second solid-liquid separation in successively, more preferably, the first solid-liquid separation uses a disc centrifuge, and the second solid-liquid separation uses a belt vacuum filter, which can further improve the final recovery rate and purity of PHA products.

Among them, the present invention does not particularly limit the conditions for the solid-liquid separation, which can be conventional operating conditions in the art, but preferably, after the solid-liquid separation, the water content of the obtained thallus precipitate is 40-90% by weight, preferably 60-80% by weight.

According to a preferred embodiment of the present invention, the first solid-liquid separation uses a disc centrifuge, and the water content of a first thallus precipitate obtained after the first solid-liquid separation is 70-85% by weight. In the second solid-liquid separation, a belt vacuum filter is used to continuously remove water from the first thallus precipitate, and the water content of a second thallus precipitate obtained after the second solid-liquid separation is 60-80% by weight.

According to the present invention, preferably, the method of the present invention includes a step of washing the thallus precipitate before breaking cell walls of the thallus precipitate. The washing can further remove impurities in the thallus precipitate, thereby further improving the purity of the PHA product. Wherein, the thallus precipitate can be washed with conventional washing solutions in the art, for example, water, physiological saline, and various buffers, for example, PBS buffer. The number of times of washing can be determined according to the impurities contained in the thallus precipitate, preferably, washing 1-5 times.

According to the present invention, the method for breaking the cell walls may be a conventional method for breaking the cell walls of bacteria in the art, for example, an organic solvent extraction method, a physical and mechanical breaking method, a surfactant method, an enzymatic method, and the like. However, the inventor of the present invention found that the organic solvent extraction method requires the addition of a third solvent component, which has the disadvantages of complicated separation process and difficult solvent recovery; physical and mechanical breaking method has problems such as large energy consumption, uneven breaking, and difficulty in amplification; The surfactant method is somewhat toxic. Therefore, based on the above problems, the inventor of the present invention proposes to break the cell walls by steaming method or enzymatic method, more preferably to break the cell walls by steaming method. In this preferred embodiment, not only the defects of the existing method for breaking cell walls are solved, but also effectively improve the purity of the final PHA product.

According to the present invention, preferably, before breaking cell walls of the thallus precipitate, the pH value of the thallus precipitate is adjusted to a suitable range of wall breaker, preferably 6-10, more preferably 7-9.

According to the present invention, the conditions for the steaming preferably include a temperature of 60-200° C., a pressure of 0.1-0.3 MPa, a stirring speed of 50-250 rpm, and a time of 0.5-4 hours; more preferably, the temperature is 90-130° C. (for example, 90° C., 100° C., 110° C., 115° C., 120° C., 125° C., 130° C.), the pressure is 0.1-0.2 MPa (for example, 0.1 MPa, 0.12 MPa, 0.14 MPa, 0.16 MPa, 0.18 MPa, 0.2 MPa), the stirring speed is 80-120 rpm, and the time is 1-2.5 hours. Within this preferred range, the recovery rate and purity of the PHA finally obtained can be further improved.

According to the present invention, the enzyme used for breaking the cells walls in the enzymatic method may be a conventional enzyme that can be used to break the cells walls of bacterial, for example, it may be at least one of lysozyme, protease and lipase.

According to the present invention, the method preferably further comprises performing impurity removal treatment on the wall-broken products before subjecting the wall-broken products to a plate and frame filtration. The inventor found that after breaking the cell walls of the thallus precipitate, the broken product mainly includes PHA, the bacterial cell walls and various intracellular components in bacteria, and the PHA and the cell walls are basically insoluble in water. According to a preferred embodiment of the present invention, a centrifugal method is used to remove impurities from the wall-broken product, and the centrifugal conditions allow impurities such as cell walls in the upper layer and PHA in the lower layer. In this way, the upper layer not only contains most of the insoluble impurities such as macromolecules, but also all soluble impurities, while the lower layer is mainly PHA insoluble substances. Wherein, the centrifuge preferably uses a disc centrifuge.

More preferably, after the centrifugation is finished, it further includes washing the PHA in the lower layer. The washing is preferably water washing, and the degree of water washing is that most impurities such as cell walls are separated, preferably 1-5 times.

According to the present invention, the method further includes drying the PHA, for example, spray drying.

According to the present invention, the PHA fermentation broth may be a fermentation broth of a conventionally microorganism that can be used to prepare PHA in the art. Preferably, the microorganism is a halophilic bacteria, for example, it may be one of *Halomonas*, according to a preferred embodiment of the present invention, the PHA fermenting strain is *Halomonas* sp.; more preferably, the PHA fermenting strain is *Halomonas* sp. TD01, its deposit number is CGMCC NO. 4353 (CN201010578858.8).

In a second aspect, the present invention provides a PHA prepared according to above method, and the PHA has a purity of at least of 90%.

EXAMPLE

The present disclosure will be described in detail below with reference to examples.

In the following examples:

The disk-type centrifuge was purchased from Nanjing Huasheng Separation Machinery Technology Co., Ltd., the model was DR 203;

The ribbon-type vacuum filter was purchased from Huzhou Nuclear Industry Huineng Environmental Protection Filtration Technology Co., Ltd., and the model was DY-500;

The plate and frame filter was purchased from Haining Yunfei Filter Equipment Co., Ltd., and the model was YF-100-1;

The surfactant sodium dodecyl sulfate (SDS) was purchased from the Yeyuan Biotechnology Co., Ltd., the product number was S15013;

Lysozyme CAS: 12650-88-3, which was purchased from Beijing Oriental Rada Biotech Co., Ltd.;

The polyhydroxyalkanoate with a particle size of 1-200 µm was purchased from Langene Biotechnology Co., Ltd., and was used for coating on a filter cloth of a plate and frame filter to form a polyhydroxyalkanoate layer;

As for the methods for measuring recovery rate and purity of PHA, please refer to the reference literature (Engineering self-flocculating *Halomonas campaniensis* for wastewater-less open and continuous fermentation).

Preparation Example

The preparation example served to illustrate the preparation of a fermentation broth of polyhydroxyalkanoate.

The *Halomonas* sp. (TD 01, the preservation number was CGMCC NO. 4353 according to the patent document CN201010578858.8) was inoculated into a seed culture medium (comprising 5 g/L of yeast powder, 10 g/L of peptone and 60 g/L of sodium chloride) to perform primary activation culture under the conditions consisting of a temperature of 37° C. and 200 rpm until $OD_{600}$ reached about 4, so as to obtain a primary seed solution;

The primary seed solution was inoculated into a seed culture medium with an inoculation amount of 10 vol %, the secondary activation culture was performed under the conditions consisting of a temperature of 37° C. and 200 rpm until $OD_{600}$ reached about 4, so as to obtain a secondary seed solution;

The secondary seed solution was subsequently inoculated into an initial fermentation medium (comprising 50 g/L of sodium chloride, 50 g/L of glucose, 15 g/L of corn steep liquor powder, 2 g/L of urea, 0.2 g/L of magnesium sulfate, 5 g/L of potassium dihydrogen phosphate, 10 mL/L of microelement mother liquid I, 3 mL/L of microelement mother liquid II, the microelement mother liquids I and II were referred in the cited patent CN201010578858.8) according to the inoculation amount of 10 vol %, the fermentation system was directly fermented without subjecting to sterilization. The control was performed such that the temperature was 37° C., the rotating speed was within a range of 600-1,000 rpm, the ventilation quantity was 0.5-2.0 vvm, and the initial dissolved oxygen was 30% or more; the sugar concentration during the fermentation process was controlled to be between 5 and 20 g/L through the replenishment material, the fermentation pH was controlled to be 8-9 by using NaOH, and the fermentation was carried out for 48 hours.

Example 1

The example served to illustrate the separation method of polyhydroxyalkanoate provided by the present disclosure.

(1) The polyhydroxyalkanoate fermentation broth prepared in the Preparation Example was subjected to centrifugal separation through a disk-type centrifuge under the separation conditions consisting of a rotation speed of 6,000 rpm and a feed rate of 60 L/min; the fermentation broth was divided into a bottom flow which was rich in fermentation thalli (with a water content of 75 wt %) and a fermentation raffinate top flow.

(2) The bottom flow which was rich in the target thalli and obtained in the step (1) was pumped into a ribbon-type vacuum filter, the thalli in the bottom flow were filtered and dried under the conditions that the pressure was 0.3 MPa and the treatment capacity was 20 kg/min, the filtered and dried thalli (with the water content of 70 wt %) entered an extraction tank for the further treatment.

(3) The thalli in the extraction tank were washed with water for 3 times, and then centrifuged to remove impurities thereof.

(4) An acid-base regulator was added into the extraction tank in the step (3) to adjust the pH value to 9, the stirring and stewing process was performed for 2 hours at the temperature of 120° C., the pressure of 0.15 MPa and the rotating speed of 100 rpm, so as to break the cell walls.

(5) The mixed liquid containing PHA after breaking the cell walls in step (4) was pumped into a disk-type centrifugal separator under the separation condition, so that the impurities such as the cell wall of the thalli was separated from the top flow, the precipitate being rich in PHA at the lower part was continuously returned to the extraction tank for repeated water washing for 2 times.

(6) The PHA mixed liquid after separating out the thallus cell wall in the step (5) was pumped into a plate and frame filter for a solid-liquid separation under the separation conditions that the temperature was 25° C., the pressure was 0.7 MPa, and the time was 5 hours. The solid particles of PHA were separated. The filter cloth of the plate and frame filter was coated with a polyhydroxyalkanoate layer with a thickness of 8 mm, and the filter cloth coated with the polyhydroxyalkanoate layer had a pore size of 2 µm.

(7) The solid PHA separated by the plate and frame filter in step (6) was subjected to the spray drying to obtain PHA dry powder, the recovery rate and purity were shown in Table 1.

Example 2

The example served to illustrate the separation method of polyhydroxyalkanoate provided by the present disclosure.

(1) The polyhydroxyalkanoate fermentation broth prepared in the Preparation Example was subjected to centrifugal separation through a disk-type centrifuge under the separation conditions consisting of a rotation speed of 5,500 rpm and a feed rate of 55 L/min; the fermentation broth was divided into a bottom flow which was rich in fermentation thalli (with a water content of 85 wt %) and a fermentation raffinate top flow.

(2) The bottom flow which was rich in the target thalli and obtained in the step (1) was pumped into a ribbon-type vacuum filter, the thalli in the bottom flow were filtered and dried under the conditions that the pressure was 0.35 MPa and the treatment capacity was 23 kg/min, the filtered and dried thalli (with the water content of 80 wt %) entered an extraction tank for the further treatment.

(3) The thalli in the extraction tank were washed with water for 2 times, and then centrifuged to remove impurities thereof.

(4) An acid-base regulator was added into the extraction tank in the step (3) to adjust the pH value to 8, the stirring and stewing process was performed for 2.5 hours at the temperature of 90° C., the pressure of 0.1 MPa and the rotating speed of 120 rpm, so as to break the cell walls.

(5) The mixed liquid containing PHA after breaking the cell walls in step (4) was pumped into a disk-type centrifugal separator under the separation condition, so that the impurities such as the cell wall of the thalli was separated from the top flow, the precipitate being rich in PHA at the lower part was continuously returned to the extraction tank for repeated water washing for 2 times.

(6) The PHA mixed liquid after separating out the thallus cell wall in the step (5) was pumped into a plate and frame filter for a solid-liquid separation under the separation conditions that the temperature was 30° C., the pressure was 0.6 MPa, and the time was 4 hours. The solid particles of PHA were separated. The filter cloth of the plate and frame filter was coated with a polyhydroxyalkanoate layer with a thickness of 10 mm, and the filter cloth coated with the polyhydroxyalkanoate layer had a pore size of 5 µm.

(7) The solid PHA separated by the plate and frame filter in step (6) was subjected to the spray drying to obtain PHA dry powder, the recovery rate and purity were shown in Table 1.

Example 3

The example served to illustrate the separation method of polyhydroxyalkanoate provided by the present disclosure.

(1) The polyhydroxyalkanoate fermentation broth prepared in the Preparation Example was subjected to centrifugal separation through a disk-type centrifuge under the separation conditions consisting of a rotation speed of 5,000 rpm and a feed rate of 50 L/min; the fermentation broth was divided into a bottom flow which was rich in fermentation thalli (with a water content of 70 wt %) and a fermentation raffinate top flow.

(2) The bottom flow which was rich in the target thalli and obtained in the step (1) was pumped into a ribbon-type vacuum filter, the thalli in the bottom flow were filtered and dried under the conditions that the pressure was 0.4 MPa and the treatment capacity was 25 kg/min, the filtered and dried thalli (with the water content of 60 wt %) entered an extraction tank for the further treatment.

(3) The thalli in the extraction tank were washed with water for 2 times, and then centrifuged to remove impurities thereof.

(4) An acid-base regulator was added into the extraction tank in the step (3) to adjust the pH value to 7, the stirring and stewing process was performed for 1 hours at the temperature of 130° C., the pressure of 0.2 MPa and the rotating speed of 80 rpm, so as to break the cell walls.

(5) The mixed liquid containing PHA after breaking the cell walls in step (4) was pumped into a disk-type centrifugal separator under the separation condition, so that the impurities such as the cell wall of the thalli was separated from the top flow, the precipitate being rich in PHA at the lower part was continuously returned to the extraction tank for repeated water washing for 2 times.

(6) The PHA mixed liquid after separating out the thallus cell wall in the step (5) was pumped into a plate and frame filter for a solid-liquid separation under the separation conditions that the temperature was 35° C., the pressure was 0.65 MPa, and the time was 3 hours. The solid particles of PHA were separated. The filter cloth of the plate and frame filter was coated with a polyhydroxyalkanoate layer with a thickness of 12 mm, and the filter cloth coated with the polyhydroxyalkanoate layer had a pore size of 10 µm.

(7) The solid PHA separated by the plate and frame filter in step (6) was subjected to the spray drying to obtain PHA dry powder, the recovery rate and purity were shown in Table 1.

Example 4

The example served to illustrate the separation method of polyhydroxyalkanoate provided by the present disclosure.

(1) The polyhydroxyalkanoate fermentation broth prepared in the Preparation Example was subjected to centrifugal separation through a disk-type centrifuge under the separation conditions consisting of a rotation speed of 4,000 rpm and a feed rate of 50 L/min; the fermentation broth was divided into a bottom flow which was rich in fermentation thalli (with a water content of 90 wt %) and a fermentation raffinate top flow.

(2) The bottom flow which was rich in the target thalli and obtained in the step (1) was pumped into a ribbon-type vacuum filter, the thalli in the bottom flow were filtered and dried under the conditions that the pressure was 0.5 MPa and the treatment capacity was 20 kg/min, the filtered and dried thalli (with the water content of 65 wt %) entered an extraction tank for the further treatment.

(3) The thalli in the extraction tank were washed with water for 2 times, and then centrifuged to remove impurities thereof.

(4) An acid-base regulator was added into the extraction tank in the step (3) to adjust the pH value to 6, the stirring and stewing process was performed for 4 hours at the temperature of 50° C., the pressure of 0.1 MPa and the rotating speed of 250 rpm, so as to break the cell walls.

(5) The mixed liquid containing PHA after breaking the cell walls in step (4) was pumped into a disk-type centrifugal separator under the separation condition, so that the impurities such as the cell wall of the thalli was separated from the top flow, the precipitate being rich in PHA at the lower part was continuously returned to the extraction tank for repeated water washing for 2 times.

(6) The PHA mixed liquid after separating out the thallus cell wall in the step (5) was pumped into a plate and frame filter for a solid-liquid separation under the separation conditions that the temperature was 40° C., the pressure was 0.8 MPa, and the time was 2 hours. The solid particles of PHA were separated. The filter cloth of the plate and frame filter was coated with a polyhydroxyalkanoate layer with a thickness of 14 mm, and the filter cloth coated with the polyhydroxyalkanoate layer had a pore size of 1 µm.

(7) The solid PHA separated by the plate and frame filter in step (6) was subjected to the spray drying to obtain PHA dry powder, the recovery rate and purity were shown in Table 1.

Example 5

The example served to illustrate the separation method of polyhydroxyalkanoate provided by the present disclosure.

(1) The polyhydroxyalkanoate fermentation broth prepared in the Preparation Example was subjected to centrifugal separation through a disk-type centrifuge under the separation conditions consisting of a rotation speed of 7,000 rpm and a feed rate of 50 L/min; the fermentation broth was divided into a bottom flow which was rich in fermentation thalli (with a water content of 60 wt %) and a fermentation raffinate top flow.

(2) The bottom flow which was rich in the target thalli and obtained in the step (1) was pumped into a ribbon-type vacuum filter, the thalli in the bottom flow were filtered and dried under the conditions that the pressure was 0.5 MPa and the treatment capacity was 20 kg/min, the filtered and dried thalli (with the water content of 50 wt %) entered an extraction tank for the further treatment.

(3) The thalli in the extraction tank were washed with water for 2 times, and then centrifuged to remove impurities thereof.

(4) An acid-base regulator was added into the extraction tank in the step (3) to adjust the pH value to 10, the stirring and stewing process was performed for 0.5 hour at the temperature of 200° C., the pressure of 0.3 MPa and the rotating speed of 120 rpm, so as to break the cell walls.

(5) The mixed liquid containing PHA after breaking the cell walls in step (4) was pumped into a disk-type centrifugal separator under the separation condition, so that the impurities such as the cell wall of the thalli was separated from the top flow, the precipitate being rich in PHA at the lower part was continuously returned to the extraction tank for repeated water washing for 2 times.

(6) The PHA mixed liquid after separating out the thallus cell wall in the step (5) was pumped into a plate and frame filter for a solid-liquid separation under the separation conditions that the temperature was 15° C., the pressure was 0.2 MPa, and the time was 8 hours. The solid particles of PHA were separated. The filter cloth of the plate and frame filter was coated with a polyhydroxyalkanoate layer with a thickness of 20 mm, and the filter cloth coated with the polyhydroxyalkanoate layer had a pore size of 20 μm.

(7) The solid PHA separated by the plate and frame filter in step (6) was subjected to the spray drying to obtain PHA dry powder, the recovery rate and purity were shown in Table 1.

Example 6

The example served to illustrate the separation method of polyhydroxyalkanoate provided by the present disclosure.

The separation of polyhydroxyalkanoate was performed in accordance with the method of the Example 2, except that the ribbon-type vacuum filter in step (2) was replaced with a disk-type centrifuge, and the separation was performed in accordance with the conditions of step (1). The recovery rate and purity were shown in Table 1.

Example 7

The example served to illustrate the separation method of polyhydroxyalkanoate provided by the present disclosure.

The separation of polyhydroxyalkanoate was performed in accordance with the method of the Example 2, except that the sufficient amount of dodecylsulfonic acid was added in step (4) to maintain at room temperature and a pressure of 0.1 MPa for 4 hours, that is, the heating and pressurizing treatment was not performed. The recovery rate and purity were shown in Table 1.

Example 8

The example served to illustrate the separation method of polyhydroxyalkanoate provided by the present disclosure.

The separation of polyhydroxyalkanoate was performed according to the method of the Example 2, except that, the polyhydroxyalkanoate used for coating the polyhydroxyalkanoate layer in step (6) was the polyhydroxyalkanoate separated from the product after breaking the cell walls. The recovery and purity were shown in Table 1.

Comparative Example 1

The Comparative Example served to illustrate and compare the separation method of polyhydroxyalkanoate provided by the present disclosure.

The separation of polyhydroxyalkanoate was performed according to the method in the Example 1, except that the filter cloth used in step (6) was not coated with a polyhydroxyalkanoate layer. The recovery rate and purity were shown in Table 1.

Comparative Example 2

The Comparative Example served to illustrate and compare the separation method of polyhydroxyalkanoate provided by the present disclosure.

The separation of polyhydroxyalkanoate was performed according to the method in the Example 1, except that the filter cloth in step (6) was coated with a layer of diatomaceous earth. The recovery rate and purity were shown in Table 1.

Comparative Example 3

The Comparative Example served to illustrate and compare the separation method of polyhydroxyalkanoate provided by the present disclosure.

The extraction of PHA from the prepared fermentation broth was performed according to the method disclosed in the literature Engineering self-flocculating *Halomonas campaniensis* for wastewaterless open and continuous fermentation, *Biotechnology and Bioengineering* [J]. 2019; 116: 805-815. The recovery rate and purity were shown in Table 1.

TABLE 1

| Example Numbers | Recovery rate (%) | Purity (%) |
|---|---|---|
| Example 1 | 86 | 94 |
| Example 2 | 85 | 93 |
| Example 3 | 84 | 92 |
| Example 4 | 80 | 91 |
| Example 5 | 82 | 90 |
| Example 6 | 85 | 92 |
| Example 7 | 81 | 90 |
| Example 8 | 83 | 92 |
| Comparative Example 1 | 70 | 88 |
| Comparative Example 2 | 75 | 84 |
| Comparative Example 3 | 79 | 90 |

It can be seen from the results in Table 1 that plate and frame filtration is used instead of centrifugal separation for PHA, and the PHA layer is pre-coated on filter cloth for the plate and frame filtration, which avoids the use of multiple centrifugal separation in the prior art resulting high cost and difficult operation. In addition, the method of the present invention also has the characteristics of high recovery rate of PHA and high purity of the obtained PHA product. As shown in the examples, the recovery rate of PHA in the method of the present invention is at least 80%, and the purity of the PHA product is at least 90%; comparing Examples 1-3 with Examples 4-8, it can be seen that under more preferable conditions, the recovery rate and purity of PHA can be further improved. In addition, the preferred wall breaking method of the present invention does not introduce the third component, which further improves the purity of PHA.

Furthermore, comparing with Example 6, Example 2 adopts a preferred separation method, which can further save costs.

The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them falls into the protection scope of the present disclosure.

The invention claimed is:

1. A method for separating polyhydroxyalkanoate (PHA) comprising the following steps:
subjecting a PHA fermentation broth to solid-liquid separation to obtain a thallus precipitate;
breaking cell walls of the thallus precipitate, and subjecting obtained wall-broken products to a plate and frame filtration to obtain PHA;
wherein a filter cloth for the plate and frame filtration is pre-coated with a PHA layer and the average particle size of PHA in the PHA layer pre-coated on the filter cloth is larger than the average particle size of PHA in the wall-broken product.

2. The method according to claim 1, wherein the particle size of PHA pre-coated on the filter cloth ranges from 1 to 200 μm.

3. The method according to claim 1, wherein the thickness of the PHA layer is 1-30 mm.

4. The method according to claim 1, wherein the pore size of the filter cloth pre-coated with the PHA layer is 1-25 μm.

5. The method according to claim 1, wherein conditions of the solid-liquid separation allows that a water content of the thallus precipitate is 40-90% by weight.

6. The method according to claim 1, wherein the solid-liquid separation includes a first solid-liquid separation and a second solid-liquid separation.

7. The method according to claim 6, wherein a disc centrifuge is used for the first solid-liquid separation, and a belt vacuum filter is used for the second solid-liquid separation.

8. The method according to claim 1, wherein the method further includes a step of washing the thallus precipitate before breaking cell walls of the thallus precipitate.

9. The method according to claim 1, wherein a method for breaking cell walls of the thallus precipitate comprises: adjusting pH of the thallus precipitate to 6-10, and then steaming to break the cell walls.

10. The method according to claim 9, wherein conditions for the steaming include: a temperature of 60-200° C., a pressure of 0.1-0.3 MPa, a stirring speed of 50-250 rpm, and a time of 0.5-4 hours.

11. The method according to claim 1, wherein the method further comprises performing impurity removal treatment on the wall-broken products before subjecting the wall-broken products to the plate and frame filtration.

12. The method according to claim 11, wherein the impurity removal treatment includes: subjecting the wall-broken products to a centrifugal treatment, and conditions of the centrifugal treatment allow that the impurities are in upper layer and the PHA is in lower layer, and then washing the PHA in the lower layer.

13. The method according to claim 1, wherein conditions of the plate and frame filtration include: a temperature of 10-40° C., a pressure of 0.2-0.8 MPa, and a time of 1-8 hours.

14. The method according to claim 1, wherein the method further comprises subjecting the PHA to a spray drying.

* * * * *